United States Patent [19]

Yoshioka et al.

[11] Patent Number: 5,229,282
[45] Date of Patent: Jul. 20, 1993

[54] PREPARATION OF BIOSENSOR HAVING A LAYER CONTAINING AN ENZYME, ELECTRON ACCEPTOR AND HYDROPHILIC POLYMER ON AN ELECTRODE SYSTEM

[75] Inventors: Toshihiko Yoshioka, Osaka; Mariko Kawaguri, Moriguchi; Shiro Nankai, Hirataka, all of Japan

[73] Assignee: Matsushita Electric Industrial Co., Ltd., Osaka, Japan

[21] Appl. No.: 617,886

[22] Filed: Nov. 26, 1990

[30] Foreign Application Priority Data

Nov. 24, 1989 [JP] Japan ................................ 1-305455

[51] Int. Cl.$^5$ ................. C12N 11/02; C12N 11/12; C12N 11/04; C12M 1/40
[52] U.S. Cl. ......................... 435/177; 435/4; 435/14; 435/176; 435/179; 435/182; 435/817; 435/288; 204/403
[58] Field of Search ............. 435/174, 176, 179, 180, 435/182, 817, 4, 14, 288; 204/403

[56] References Cited

U.S. PATENT DOCUMENTS 4,418,148  11/1983  Oberhardt ........................ 435/179
4,897,173   1/1990  Nankai et al. ................. 435/817 X

OTHER PUBLICATIONS

Miyamaki, et al., Biochimica et Biophysica Acta, vol. 838, 1985, pp. 60-68.

Primary Examiner—David M. Naff
Attorney, Agent, or Firm—Wenderoth, Lind & Ponack

[57] ABSTRACT

The present invention relates to a process of preparation of a biosensor comprising forming an electrode system mainly containing carbon on an insulating base plate, treating the surface of electrode system with an organic solvent, and then arranging a reaction layer on the electrode system to give a unified element. The reaction layer contains an enzyme, electron acceptor and a hydrophilic polymer. Treatment with the organic solvent improves adhesion of the reaction layer to the electrode system. The electrode system contains a working electrode and a counter electrode. The electrode system is formed from a carbon paste containing a resin binder. Treatment is preferably carried out by wiping the surface of the electrodes with a material impregnated by the organic solvent.

8 Claims, 4 Drawing Sheets

PREPARATION OF BIOSENSOR HAVING A LAYER CONTAINING AN ENZYME, ELECTRON ACCEPTOR AND HYDROPHILIC POLYMER ON AN ELECTRODE SYSTEM

FIELD OF THE INVENTION

The present invention relates to a process for preparation of biosensor by which a specific component in various sample solutions from the living body can be quantitatively determined in a rapid and easy way with high accuracy.

BACKGROUND OF THE INVENTION

In recent years, various biosensors utilizing a specific catalytic action possessed by enzyme have been developed and in particular, it has been attempted to apply biosensors to the clinical field, and biosensors which can provide rapid assay with good accuracy have been desired.

Taking a glucose sensor as an example, diabetes has markedly increased nowadays and for measurement and control of blood glucose concentration, it takes a very long time, since blood is centrifuged and plasma is provided for the measurement as is conventionally done. Thus, a sensor which can make measurement with whole blood is required. As a handy type, there is a stick-like support having provided thereon a carrier containing an enzyme capable of reacting only with glucose and a dye which changes color upon enzyme reaction or by the product of the enzyme reaction, like a test sheet used for inspection of urine. The stick takes the system that blood is dropped onto the carrier and after a definite period of time, a change of the dye is visually or optically determined. However, interference is serious because of colored matters in blood, resulting in poor accuracy.

Now, a multilayer type analysis carrier as shown in FIG. 1 is proposed (Japanese Utility Model Application Laid-Open No. 54-178495). The carrier has the construction comprising a transparent support 51 having provided thereon, in order, a reagent layer 52, a developing layer 53, a waterproofing layer 54 and a filtering layer 55. The measurement takes the following system: when a blood sample is dropped from the upside, solid components in blood such as red blood cells, platelets, etc. are removed by the filtering layer 55, the blood uniformly permeates into the developing layer 53 through a hole 56 in the waterproofing layer and a reaction proceeds in the reagent layer 52. After completion of the reaction, a light is irradiated from the arrow direction through the transparent support 51, whereby a substrate concentration is determined by colorimetry. The system takes a complicated construction as compared to the conventional handy stick-like carrier but its accuracy has improved because blood cells are removed, etc. However, it takes a long time for the permeation of blood and the reaction so that the waterproofing layer 54 that prevents drying of the sample is required. In addition, incubation at a high temperature is required for accelerating the reaction. Thus, the system involves problems that apparatuses and carriers become complicated.

On the other hand, as the system for quantitative assay of a specific component in a sample such as blood, etc. from the living body with high accuracy without performing operations such as dilution, agitation, etc. of the sample solution, a biosensor as shown in FIG. 2 has been proposed (for example, Japanese Patent Application Laid-Open No. 59-166852). The biosensor comprises an insulating base plate 63 having embedded therein a working electrode 64 and a counter electrode 65 made of platinum, etc., having leads 61 and 62, respectively, and the exposed areas of these electrodes are covered with a porous material 66 having carried thereon an oxidoreductase and an electron acceptor. When a sample solution is dropped onto the porous material, the oxidoreductase and the electron acceptor are dissolved in the sample solution, whereby an enzyme reaction proceeds with a substrate in the sample solution and the electron acceptor is reduced. After completion of the reaction, the reduced electron acceptor is electrochemically oxidized and a substrate concentration in the sample is determined from a current level for the oxidation obtained in this case.

In such a construction, however, the electrodes require operations such as washing, etc., while the porous material can be exchanged for every assay thereby to readily provide for measurement. On the other hand, if it is possible to dispose the apparatus including the electrode system for every measurement, operations for the measurement become extremely simple but from aspects of electrode materials such as platinum, etc., construction and the like, the apparatus is very expensive unavoidably. For the construction of platinum electrodes, the sputtering method or the deposition method can also be used but production costs increase.

As a disposable system including the electrode system, a biosensor described in Japanese Patent Application Laid-Open No. Hei. 01-291153 has been proposed.

As shown in FIGS. 3 and 4 in this bio-sensor electric leads 2 and 3, electrodes consisting of a working electrode 4 and a counter electrode 5, and an insulative layer 6 are formed on an insulative base plate 1 by means of screen printing and the like, and an enzyme reaction layer 14 consisting of a hydrophilic polymer, an oxidoreductase and an electron acceptor is formed on the electrodes, which are integrated with a spacer 10 and a cover 11. When a sample liquid is introduced onto the enzyme reaction layer 14 from a sample feed 12, the air of the reaction layer 14 is removed from the air outlet 13, and the reaction layer 14 is rapidly filled with the sample liquid. The reaction layer 14 is dissolved with the sample liquid, the enzyme reaction progresses between oxidoreductase and the substrate in the sample liquid, and the electron acceptor is reduced. After the enzyme reaction is completed, the reduced electron acceptor is electrochemically oxidized to determine the substrate concentration in the sample liquid according to the value of the electric current at this oxidation.

It was difficult to produce a biosensor having an even quality in the above constitution, because the surface state of the electrode system produced according to a method such as screen printing which is usually adopted to produce a disposable biosensor economically becomes finely varied to give an uneven sensor response. Additionally, according to the above method the wettability of surface of the base plate containing the electrodes is so much worse that a solution containing an enzyme is repelled on the electrodes, when coated or spread on the electrodes, so as to hardly form the reaction layer often.

Therefore, as a method of preparing sensors for measuring a specific component in a biological liquid sample such as blood or the like in a simple and rapid way.

with high accuracy, a method is desired by which an even reaction layer can be easily formed. Further, it is desired that the biosensor has a good storage stability.

SUMMARY OF THE INVENTION

The present invention provides a preparation of a disposable biosensor improved in the evenness among each individual biosensor, responsibility, accuracy and so on by treating the surface of electrodes of the aforementioned conventional disposable biosensor with an organic solvent in the course of the preparation thereof to remove the oxide film or other dirt formed over the electrodes.

DISCLOSURE OF THE INVENTION

The present invention relates to a process for preparing a biosensor which comprises arranging an electrode system consisting of a least a working electrode and a counter electrode onto an insulating base plate, treating the surface of at least said electrodes for measurement, preferably the whole electrode system with an organic solvent, and then applying a reaction layer onto the treated electrodes.

The surface of the electrodes can be made even and clean by this treatment with an organic solvent, as the result of which the adhesion of the reaction layer onto the surface of the electrode is increased, and the release can be prevented. Further, the arrangement of the reaction layer on the electrode can be made easy, because the wettability of the electrodes is improved thereby, and the formation of bubble can be prevented because the sample liquid can be smoothly introduced onto the electrode. Therefore, a biosensor excellent in a reliability can be obtained according to the present invention.

Furthermore, it becomes easy to minimize unevenness among biosensors by increasing the uniformity of each individual biosensor when it is prepared. Additionally, an oxide film over the electrodes can be easily removed by the treatment with the organic solvent, so that a biosensor can be obtained, by which a substrate concentration can be determined with an excellent responsibility and accuracy.

According to the biosensor of the present invention an adverse influence to the electrodes by solid ingredients such as protein, blood red cell and the like in a blood sample can be prevented by arranging a layer containing a hydrophilic polymer on the electrode. Further, the inactivation of an electrode surface by oxidation can be prevented by the treatment with an organic solvent.

BEST MODES FOR PRACTICING THE INVENTION

EXAMPLE 1

In the following explanatory drawings in the examples, the same numbering is used for common elements and their explanation is in part omitted.

Figure 5:
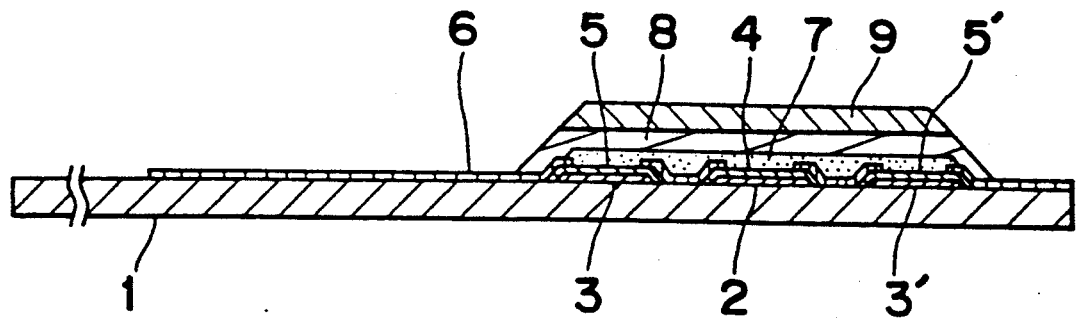
FIG. 5 is a schematic sectional view of one embodiment of a biosensor of the present invention.

As one embodiment of the biosensor a glucose sensor is illustrated. FIG. 5 is a schematic sectional view of a glucose sensor, which was prepared as one example of biosensor according to the present invention.

Hereafter a process for preparing the sensor is described. Silver paste was printed on an insulating base plate (1) composed of polyethylene terephthalate by means of screen printing to form leads (2), (3), (3'). Next, conductive carbon paste containing a resin binder was printed thereon. By drying with heating, the electrode system consisting of a working electrode (4) and a counter electrode (5), (5') was formed. Furthermore, an insulating paste was printed so as to partly cover the electrode system to make the exposed area of the electrodes definite, and covered unnecessary part of the leads. By a heat treatment, an insulating layer (6) was formed.

Next, the exposed area of the electrode system (4), (5), (5') was polished and then heat-treated at 100° C. for 4 hours in the air. The working electrode and the counter electrode were then lightly wiped with a gauze impregnated with ethyl alcohol as an organic solvent, and dried.

After the electrode surface was thus treated with ethyl alcohol, 0.5% aqueous solution of carboxymethyl cellulose (herein after simply referred to as CMC) as the hydrophilic high molecular substance (simply referred to as hydrophilic polymer hereinafter) was spread onto the electrodes and dried to form a CMC layer. In case that the CMC layer was formed on the electrode system which was not wiped with a gauze impregnated with ethyl alcohol, release of the CMC layer was observed after the layer was dried, whereas in case that the electrode system was wiped therewith the affinity between the surface of the electrode and CMC layer was increased to enable to form a stable layer. Further, the removal of carbon fine particles caused by polishing became possible, so the insulation between the electrodes could be retained.

A solution of glucose oxidase (simply referred to as GOD hereinafter) as the enzyme in phosphate buffer solution (pH value=5.6) or in water was spread thereon and dried to form a CMC-GOD layer (7). In this case, CMC and GOD formed a thin layer having a thickness of several microns in a partly mixed state. Further, 0.5% polyvinylpyrrolidone (hereinafter simply referred to as PVP) solution in ethyl alcohol was spread so as to fully cover the first layer composed of this CMC-GOD layer and dried to form a PVP layer (8). A mixture of microcrystalline potassium ferricyanide as an electron acceptor and 0.5% solution of lecithin as a surface active agent in toluene was dropped and spread onto the PVP layer and dried to form a potassium ferricyanide-lecithin layer (9). A human whole blood 5 μl was added dropwise onto the glucose sensor prepared according to the above method. Applying a pulse voltage of +0.6 V (based on the counter electrode) to the electrode for measurement in the anode direction one minute after, a response current was measured after 5 seconds.

Figure 6:
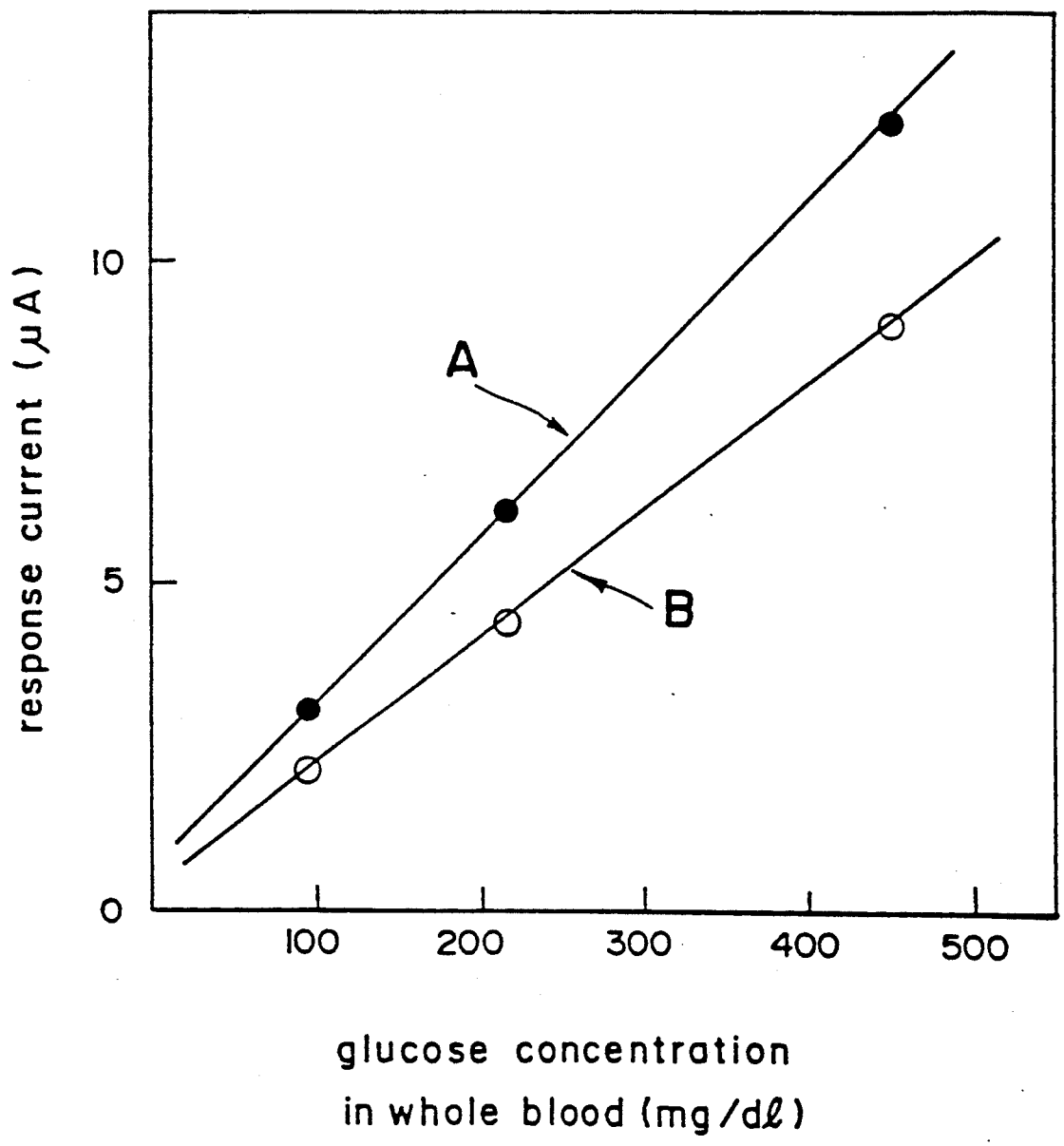
FIG. 6 is a graph illustrating a response characteristic.

The sample liquid being added, the potassium ferricyanide-lecithin layer (9) was first dissolved into the sample liquid. Comparatively large components such as a blood cell and the like in the sample liquid were filtered by the PVP layer (8), and the sample liquid permeated to CMC-GOD layer (7), on which the glucose in the sample liquid was oxidized and simultaneously the potassium ferricyanide was reduced to potassium ferrocyanide. The aforementioned the pulse electric voltage was applied to determine the oxidizing current corresponding to the concentration of the generated potassium ferrocyanide. The current value corresponds to the concentration of glucose, i.e. substrate. A good linear relation was observed up to the glucose concentration in the whole blood being 450 mg/dl (0.025 mol/l) or more, and when this test was performed with 30 piece of the glucose sensor having the same specification to the same whole blood sample, the variation coefficient was as good as about 4%. Using a biosensor prepared according to the present invention and one prepared according to the same manner except the treatment with an organic solvent was omitted a response characteristic in a whole blood sample was determined respectively, and the results were shown in FIG. 6, in which A and B indicated the results obtained from the biosensor treated with organic solvent and results from the biosensor without the treatment respectively. As apparent from FIG. 6, the former (A) is higher than the latter (B) in the sensitivity.

The above results are due to evenness and activation of the electrode surface by the removal of an oxide film and clinging impurities thereon by the treatment with an organic solvent. Another reason is considered that it is prevented the direct influence to the response which is caused by the absorption of solid components such as proteins, red blood cell and the like in the sample liquid onto the surface of the electrodes.

When a response current was determined using a glucose standard solution as a sample liquid, a good linear relation could be obtained up to a high concentration, 900 mg/dl (0.05 mol/l) or more.

EXAMPLE 2

Figure 1:
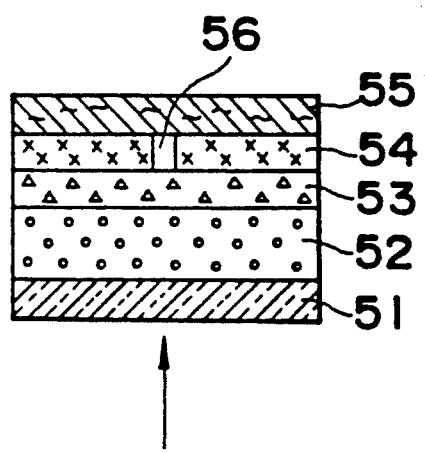
FIGS. 1 and 2 are illustrative drawings showing examples of conventional glucose sensors.
Figure 2:
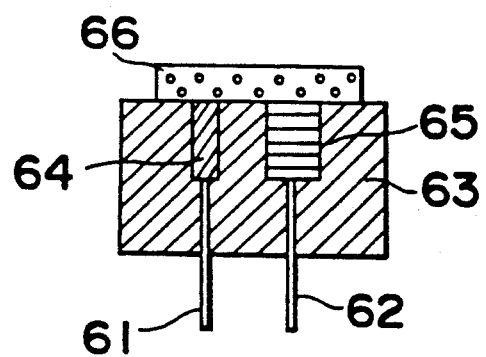
Figure 3:
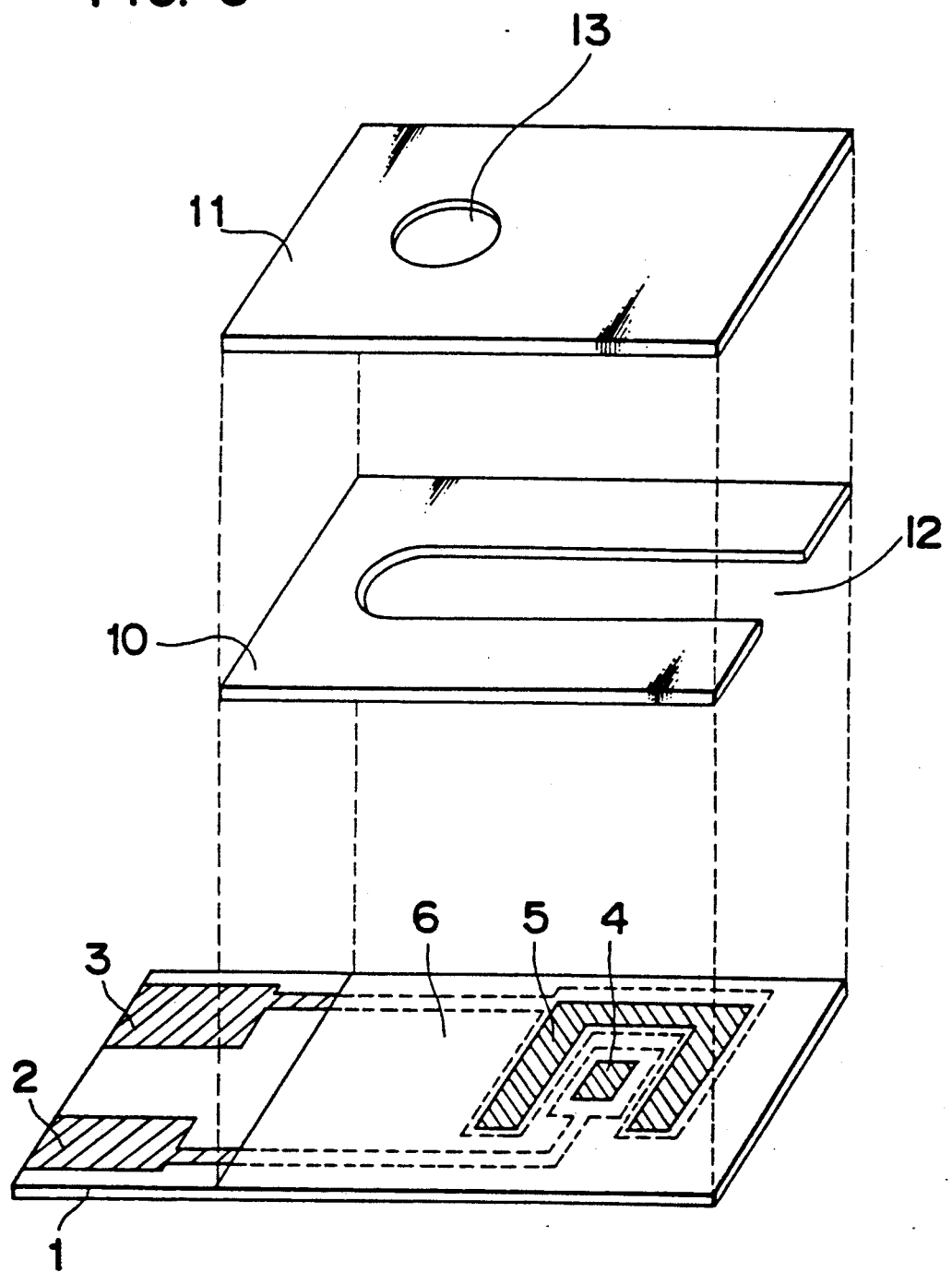
FIG. 3 shows a perspective view of a disassembled conventional disposable biosensor.
Figure 4:
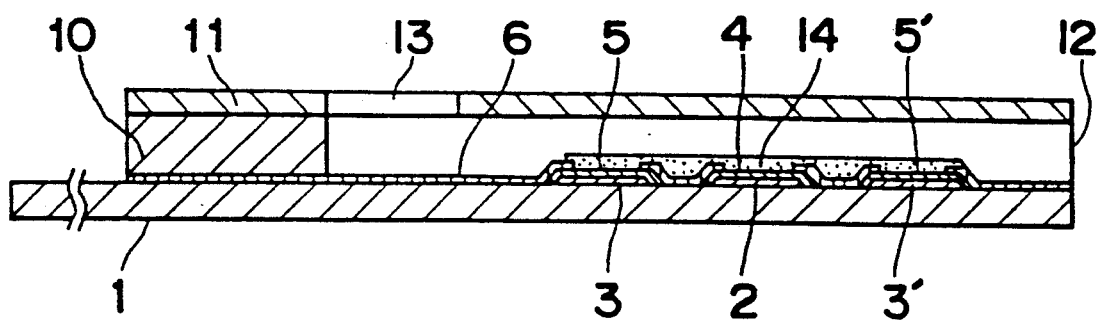
FIG. 4 is a schematic sectional view of FIG. 3.

The same electrode portion as illustrated in FIG. 3 was formed on an insulating base plate consisting of polyethylene terephthalate by means of screen printing in a manner similar to the Example 1. The exposed portions (4) and (5) were polished by a felt impregnated with methyl alcohol, and then dried. A polishing material having a high liquid retention as a felt being used, the polishing and the treatment with an organic solvent can be simultaneously achieved by the impregnation of the solvent into the polishing material, so the biosensor can be economically prepared. This process can also prevent the carbon particle of the electrode from scattering at polishing. Further, a CMC-GOD layer, a PVP layer and a potassium ferricyanidelecithin layer were formed in a manner similar to the Example 1.

Onto the glucose sensor prepared according to the above process a glucose standard solution 10 μl was added dropwise as a sample solution, after one minute a pulse voltage of +0.5 V was applied between the electrodes, and then the current after 5 seconds was measured. Similar to the result from the Example 1, a response current corresponding to the glucose concentration was obtained. The good linear relation was also obtained up to the concentration of 900 mg/dl (0.05 mol/l) or more in this Example. In case a whole blood was used as a sample liquid an excellent reproducibility in the response was obtained as in the Example 1.

EXAMPLE 3

According to the same manner as in the Example 1 the several processes for the formation of the insulating layer (6) were repeated, the exposed portions (4) and (5) were polished, and then the obtained substance was subjected to heat treatment at 100° C. for 4 hours in atmosphere. After this treatment the electrode system was exposed over diethyl ether gas circumstances for 60 minutes. Onto the treated electrode system an aqueous solution of CMC (0.5 wt %) containing GOD and potassium ferricyanide is added dropwise and then dried at 40° C. for 10 minutes in a warm air drier to form an enzyme reaction layer to give a glucose sensor.

According to this method, the process for the preparation of the glucose sensor can be simplified by the one time addition of a mixed solution of a hydrophilic polymer, an oxidoreductase and an electron acceptor, and drying it. A temperature for the drying is preferably 20°–80° C. in view of maintenance of enzyme activity and short time drying.

Onto the glucose sensor obtained a whole blood 5 μl was dropped, after one minute a pulse voltage of +0.5 V based on the counter electrode toward the anode was applied on the electrode for measurement, and then the current after 5 seconds was measured. A response current corresponding to the glucose concentration in the whole blood was obtained. Further, when the same sample liquid was dropped thereon, and the voltage was applied after 30 seconds, almost the same response current was observed after one minute. The ground that the above result was obtained was that the reaction layer contained GOD and potassium ferricyanide in mixture, so that the reaction rapidly progressed due to the homogenous solution after the both were dissolved in the sample liquid.

EXAMPLE 4

According to the manner similar to the Example 1, the electrode system was formed on the insulating base plate, and after the polishing and heat treatment the surface of the electrode system was treated with ethyl alcohol. An aqueous solution of CMC (0.5 wt %) as a hydrophilic polymer was spread over the electrodes and dried to form a CMC layer. Onto the CMC layer obtained an aqueous solution of CMC 0.5 wt % containing GOD and potassium ferricyanide was dropped, dried at 40° C. for 10 minutes in a warm air drier to form an enzyme reaction layer to give a glucose sensor.

The enzyme and the electron acceptor could be concentrated upon the working electrode by dropping a solution containing an enzyme on the hydrophilic polymer layer as aforementioned, because the GOD and potassium ferricyanide concentrated upon the dropping point without broadly spreading over the CMC layer due to the rapid absorption of water into the CMC layer, which was a solvent for the GOD, potassium ferricyanide and CMC lately added. As such the GOD and potassium ferricyanide could be concentrated onto the electrode for measurement of the sensor by dropping the mixed aqueous solution containing the GOD after the CMC layer was composed, and it became possible to prepare a sensor by which a stable response was obtained by developing a minimum amount of sample to be needed.

Onto the glucose sensor obtained according to the above process a whole blood 5 μl was dropped as a sample liquid, and then after one minutes a pulse voltage of +0.5 V based on the counter electrode toward the anode was applied to the electrode for measurement. When the electric current after 5 seconds was determined, a response current value corresponding to the glucose concentration in the whole blood was obtained. When this test was performed with 30 pieces of the sensor to the same whole blood sample, the variation coefficient was as good as about 3%.

Though in the above Examples there are illustrated glucose sensors, the present invention should not be construed limitedly to the glucose sensors, but applicable to any system to which an oxidoreductase relates.

As the treatment with an organic solvent there are exemplified the application of ultrasonic wave (frequency: typically 26 kHz) to the electrode as immersed in the organic solvent for several minutes, immersion of the electrode into an organic solvent for about 2 hours and the like, by which a similar effect can be achieved.

The organic solvent usable in the present invention may be selected from any solvents which do not adversely affect, for instance, dissolve, swell or soften the base plate or the electrode system. Easily volatile solvents are preferable. As a preferable solvent there are exemplified alcohols such as methyl alcohol, ethyl alcohol, isopropyl alcohol and the like; ethers such as diethyl ether; hydrocarbon, such as n-hexane, heptane, cyclohexane, and the like.

Though CMC and PVP are used as a hydrophilic polymer in the above Examples, it should not be construed limitedly to these polymers. As a suitable hydrophilic polymer there are included polymers such as polyvinyl alcohol or copolymer thereof, cellulose derivatives, gelatine or its derivatives, starch or its derivatives, homo or copolymer containing a residue derived from an unsaturated monomer such as vinyl pyrrolidones, (meth)acrylic acid, salts thereof, maleic anhydride, salts thereof, (meth)acryl amide or salts thereof and the like, by which similar effect is achieved.

The solution containing one or more hydrophilic polymer as aforementioned may be applied in a suitable concentration and dried to form a hydrophilic polymer layer on the electrode in a necessary thickness.

Though in the above Examples the lecithin is used for dispersing the electron acceptor, any other dispersant can be used providing that it does not adversely affect the enzyme activity. As examples of the dispersant usable in the present invention includes a nonionic surface active agent such as polyoxyethylene alkylphenyl ether, polyoxyethylene alkyl ether, polyethylene glycol alkyl ester, sorbitan fatty acid ester, polyoxyethylene sorbitan fatty acid ester, glycerine fatty acid ester, and the like; an anionic surface active agent such as fatty acid such as oleic acid or salts thereof, alkylbenzenesulfonate, alkyl sulfate, and the like.

There is described a glucose sensor comprising two electrodes, a working electrode and a counter electrode in the above Examples, but the sensor may contain additional electrode, i.e. a reference electrode, by which more accurate measurement can be achieved.

As an electron acceptor there are exemplified p-benzoquinone, phenazine methosulfate, ferrocene and the like other than the aforementioned potassium ferricyanide.

As a oxidoreductase there are exemplified alcohol oxidase, cholesterol oxidase, xanthine oxidase, amino acid oxidase, and the like can be used other than the glucose oxidase.

INDUSTRIAL APPLICABILITY

According to the present invention a biosensor improved in the responsibility and accuracy, and evenness among each individual biosensor can be obtained, and as the obtained biosensor is usable to assay defined components in various living samples rapidly and accurately, it can be used for clinical test with great utility.

What is claimed is:

1. A process for preparation of a biosensor for determining electrochemically a change of substance concentration caused by reaction of an enzyme, an electron acceptor and a sample liquid, which consists essentially of arranging an electrode system made of carbon as a main component, wherein the carbon is provided by a carbon paste containing a resin binder and said electrode system consisting essentially of at least a working electrode and a counter electrode on an insulating base plate, contacting the surface of the working electrode and counter electrode with an organic solvent by wiping the surface of the electrodes with a material impregnated by an organic solvent, and arranging a reaction layer consisting of at least an enzyme, an electron acceptor and a hydrophilic polymer on the electrode system, said contacting with an organic solvent improving adhesion of the reaction layer to the electrode system.

2. The process for preparation of a biosensor of claim 1, in which said enzyme is an oxidoreductase.

3. The process for preparation of a biosensor of claim 1, in which the electrode system consisting essentially of carbon is applied on an insulating base plate by screen printing.

4. The process for preparation of a biosensor of claim 1, in which the organic solvent is selected from the group consisting of methanol, ethanol, isopropyl alcohol, diethyl ether, n-hexane, heptane, and cyclohexane.

5. The process for preparation of a biosensor of claim 2, in which there is formed a first layer containing a hydrophilic polymer and an oxidoreductase on the electrodes contacted with an organic solvent, formed a second layer of a hydrophilic polymer by applying a solution of a hydrophilic polymer in an organic solvent on the first layer, and then formed a third layer containing an electron acceptor by applying a dispersion of the electron acceptor in an organic solvent on the second layer.

6. The process for preparation of a biosensor of claim 2, in which the reaction layer is formed by applying a solution comprising a hydrophilic polymer, an oxidoreductase, and an electron acceptor on the electrodes contacted with an organic solvent.

7. The process for preparation of a biosensor of claim 2, in which the reaction layer is formed by forming a layer containing a hydrophilic polymer on the electrodes contacted with an organic solvent, and applying a solution containing an oxidoreductase and an electron acceptor to said layer containing a hydrophilic polymer.

8. The process for preparation of a biosensor of claim 5, 6 or 7, in which the hydrophilic polymer of the reaction layer is selected from the group consisting of cellulose derivatives, gelatine or its derivatives, starch or its derivatives, homo or copolymer containing a residue derived from an unsaturated monomer selected from the group consisting of vinyl pyrrolidones, (meth)acrylic acid, salts thereof, maleic anhydride, salts thereof, (meth)acryl amide and salts thereof.

* * * * *